United States Patent
Gill

(10) Patent No.: US 7,329,262 B2
(45) Date of Patent: Feb. 12, 2008

(54) STEREOGUIDE FOR CLAMPING NEUROSURGICAL INSTRUMENTS

(75) Inventor: Steven Streatfield Gill, Bristol (GB)

(73) Assignee: Renishaw PLC (GB)

( * ) Notice: Subject to any disclaimer, the term of this patent is extended or adjusted under 35 U.S.C. 154(b) by 0 days.

(21) Appl. No.: 10/507,360

(22) PCT Filed: Mar. 11, 2003

(86) PCT No.: PCT/GB03/01027

§ 371 (c)(1),
(2), (4) Date: Jan. 28, 2005

(87) PCT Pub. No.: WO03/077784

PCT Pub. Date: Sep. 25, 2003

(65) Prior Publication Data

US 2005/0125007 A1    Jun. 9, 2005

(30) Foreign Application Priority Data

Mar. 12, 2002 (GB) ................... 0205773.5

(51) Int. Cl.
| A61F 5/00 | (2006.01) |
| A61B 19/00 | (2006.01) |
| A61B 1/00 | (2006.01) |
| A61B 5/04 | (2006.01) |
| A61B 18/14 | (2006.01) |
| A61M 5/00 | (2006.01) |

(52) U.S. Cl. .............. 606/130; 606/96; 606/97; 606/98; 606/129; 600/102; 600/378; 600/372; 600/417; 604/114; 604/116; 248/82

(58) Field of Classification Search ............... 606/130, 606/129, 96–98, 1; 604/116, 114; 600/114, 600/417, 102, 378; 248/82
See application file for complete search history.

(56) References Cited

U.S. PATENT DOCUMENTS

| 3,460,537 | A | | 8/1969 | Zeis |
| 4,504,269 | A | * | 3/1985 | Durand ..................... 604/272 |
| 5,380,290 | A | | 1/1995 | Makower |
| 5,643,286 | A | * | 7/1997 | Warner et al. .............. 606/130 |
| 6,011,996 | A | * | 1/2000 | Gielen et al. ............... 607/116 |
| 6,413,263 | B1 | * | 7/2002 | Lobdill et al. .............. 606/129 |
| 7,033,326 | B1 | * | 4/2006 | Pianca et al. ............... 600/585 |

FOREIGN PATENT DOCUMENTS

| DE | 19906094 A1 | 9/2000 |
| GB | 2342863 A | 4/2000 |

OTHER PUBLICATIONS

Sven-Ivar Seldinger: Catheter replacement of the needle in percutaneous arteriography (a new technique). Acta Radiologica, Stockholm, 1953, 39: 368-376.*

Indigo Instruments☐☐www.indgo.com☐☐© Copyright 1997-2006, Indigo® Instruments. All Rights Reserved.*

* cited by examiner

*Primary Examiner*—(Jackie) Tan-Uyen Ho
*Assistant Examiner*—Melissa Ryckman
(74) *Attorney, Agent, or Firm*—Kohn & Associates, PLLC; Kenneth I. Kohn

(57) ABSTRACT

The present invention relates to apparatus for use in neurosurgery, and to a method of positioning neurosurgical apparatus. The stereoguide comprises first and second guide elements through which instruments are passed along an axis of insertion towards a target and a first clamp (25) having a clamping position on the axis between the guide elements and the target.

9 Claims, 3 Drawing Sheets

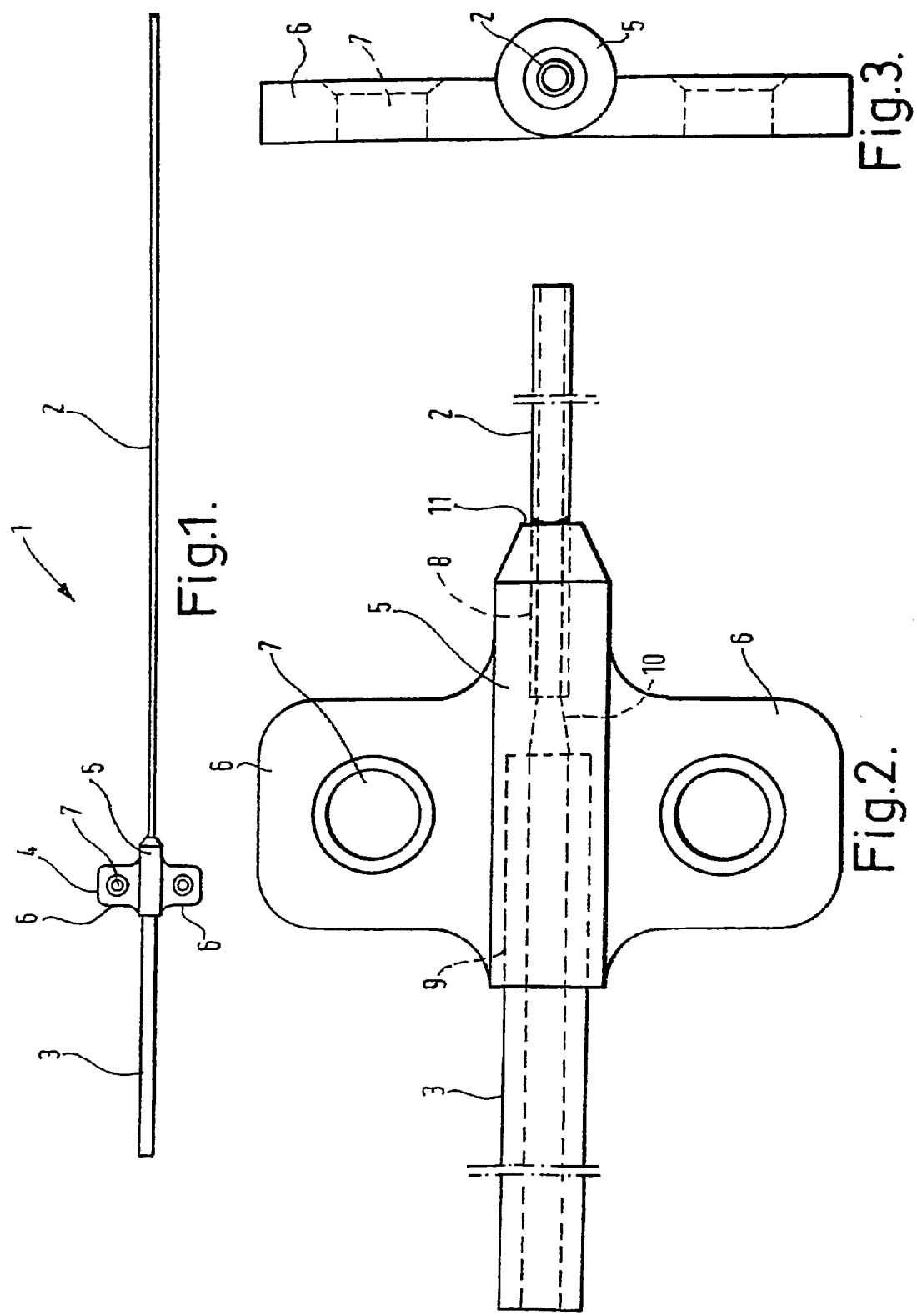

STEREOGUIDE FOR CLAMPING NEUROSURGICAL INSTRUMENTS

CROSS-REFERENCE TO RELATED APPLICATIONS

This patent application is a National Phase Concerning a Filing Under 35 U.S.C. 371, claiming the benefit of priority of PCT/GB03/01027, filed Mar. 11, 2003, which claims the benefit of priority to GB Ser. No. 0205773.5, filed Mar. 12, 2002, all of which are incorporated herein by reference.

The present invention relates to apparatus for use in neurosurgery, and to a method of positioning neurosurgical apparatus. The apparatus and method are particularly useful in stereotactically targeting treatment of abnormalities of brain function, and for the infusion of therapeutic agents directly into the brain parenchyma.

Where therapeutic agents will cause unwanted side effects if delivered to healthy parts of the brain, delivery of the agent to exactly the right place is important. Examples of treating abnormalities of brain function include the acute infusion of Gamma-amino-buturic-acid agonists into an epileptic focus or pathway to block transmission, and the chronic delivery of opiates or other analgesics can be infused directly to the peri-aqueductal grey matter or to thalamic targets for the treatment of intractable pain. Also, cytotoxic agents can be delivered directly into a brain tumour. Intraparenchymal infusion can also be used to deliver therapeutic agents to brain targets that can not be delivered systemically because they will not cross the blood-brain barrier. For example, the treatment of patients with Parkinson's disease, Alzheimer's disease, head injury, stroke and multiple sclerosis may be carried out by the infusion of neurotrophic factors to protect and repair failing or damaged nerve cells. Neurotrophins may also be infused to support neural grafts transplanted into damaged or malfunctioning areas of the brain in order restore function.

Intraparenchymal drug delivery has been demonstrated in non human primates and in rats. For intraparenchymal drug delivery to a human or non-human brain, it is proposed that a catheter be implanted, and the drug be pumped intermittently or continuously to the desired brain target. For long term drug delivery, a pump containing a reservoir would be implanted subcutaneously and the reservoir refilled as necessary percutaneously through a palpable port.

In particular, U.S. Pat. No. 6,042,579 discloses techniques for treating neurodegenerative disorders by the infusion of nerve growth factors into the brain.

It is not just catheters which can be inserted into the brain parenchyma, but also other instruments such as electrodes. Stimulating and lesioning electrodes are used in a variety of surgical procedures, including deep brain stimulation (DBS) electrodes. A surgeon wishing to stimulate or lesion a particular area of nervous tissue can target the end of an electrode to the target site so that a desired electrical current can be delivered. Numerous methods are known for targeting the electrode to the desired site including stereotactic methods.

An example of a currently used DBS electrode is supplied by Medtronic Inc. of Indianapolis, Minn. Such electrodes typically have a diameter of about 1.27 mm with four ring electrodes of the same diameter positioned at their distal end.

In order to perform neurosurgery, the surgeon needs, in the first instance, to identify the position of the desired target. This is normally achieved by fixing a stereotactic reference frame to the patient's head which can be seen on diagnostic images, and from which measurements can be made. The stereotactic frame then acts as a platform from which an instrument is guided to a desired target using a stereoguide that is set to the appropriate co-ordinates. Once an instrument is guided to the desired target, treatment can begin.

A number of difficulties are encountered in such neurosurgical procedures. Sub-optimal placement of the instrument being inserted may lead to significant morbidity or treatment failure. Brain targets for treating functional disorders are usually deeply situated and have small volumes. For example, a desired target for treating Parkinson's disease is situated in the sub-thalamic nucleus and is 3-4 mm in diameter, or an ovoid of 3-4 mm in diameter and 5-6 mm in length. Other targets such as the globus palladus or targets in the thalamus are usually no more than 1-2 mm larger. For such a small target sub-optimal placement of as little as 1 mm will not only reduce the effectiveness of the treatment, but may also induce unwanted side affects such as weakness, altered sensation, worsened speech and double vision. However, functional neurosurgical targets are often difficult or impossible to visualise on diagnostic images, and so that the actual position may need to be inferred with the reference to visible landmarks in the brain and using a standard atlas of the brain to assist the process. Anatomical variations between an individual and the atlas, and even between different sides of the same brain of an individual means that placement may be sub-optimal. Other reasons for sub-optimal placement may result from patient movement during image acquisition, or geometric distortion of imaging which can be intrinsic to the images method. Also, during surgery, brain shift can occur which might result from the change in the head position from that during image acquisition to the position on the operating table, from leakage of cerebrospinal fluid when a burr hole is made with a subsequent sinking of the brain, and also from the passage of the instrument through the brain. Surgeons attempt to correct these errors by performing electrophysiological studies on the patient undergoing functional neurosurgery, kept awake during the procedures.

Intraparenchymal instruments may be guided to their targets in the brain using stereotactic techniques. Typically, stereotactic localisation of a brain target is accomplished by fixing the stereotactic base ring to the skull and identifying the position of the target using imaging techniques. The position of the target is identified using three dimension co-ordinates by making measurements from radio-opaque fiducials attached to the stereotactic base ring. The stereotactic base ring may then be used as a platform from which to guide instruments to the target using a stereoguide on the stereotactic base ring that is set to the measured co-ordinates. The instrument may then be guided towards the target through the brain tissue. If the instrument is a catheter, it is preferably rigidified by the insertion of a stiff wire through its bore. Alternatively, a straight wire may be guided to the target and the catheter introduced around the wire. The instrument is inserted so that one end, the inserted end (also referred to as the distal end), is located within the brain, and the opposite end, which is the external end, (also referred to as the proximal end) remains outside the brain. Once positioned, the external end of the instrument can be fixed to the skull, and if it is in a catheter, it can be connected to a pump whereby the therapeutic agent may be administered.

Functional neurosurgical targets are deeply situated and typically at a depth of 70-80 mm from the cortical surface. This includes possible targets in the mesencephalon including the subthalamic nucleus, the substantia nigra and the pedunculor-pontine nucleus. The mesencephalon is a critical region of the brain where is it is important to minimise trauma from the passage of an electrode or catheter. It is typically at a depth of about 70-80 mm from the skull surface and is contained within a volume which has a height of approximately 20-25 mm.

The present invention seeks to optimise the placement of an instrument, and to improve the manner in which multiple instruments are inserted along the same axis.

According to a first aspect of the invention, there is provided a stereoguide comprising first and second guide elements through which instruments are passed along an axis of insertion towards a target; characterised by a first clamp having a clamping position on the axis between the guide elements and the target, or on the opposite side of the guide elements for clamping instruments passing through the guide elements.

The stereoguide guide is used to guide instruments along a defined axis so that the instrument reaches the target. The stereoguide in use is attached to a stereotactic frame.

The term "guide elements" as used herein means elements which allow the movement of instruments along the axis of insertion. The guide elements may comprise a split block having a passage way allowing instruments to move along a defined axis. Suitable guide elements are known to those skilled in the art and include those Elekta Instruments AB.

Any instrument for use in neurosurgery may be used with the stereoguide of the present invention, including catheters, electrodes such as deep brain stimulating (DBS) electrodes, guide wires and guide tubes such as those described in GB-A-2 357 700.

The axis of insertion is the axis along which instruments are passed to reach the target. The axis of insertion is defined by the position of the guide elements in accordance with standard procedures of using the stereotactic frame.

The term "clamp" as used herein refers to a clamp which can clamp the instrument passing through the guide elements and prevent movement of the instrument along the axis of insertion (i.e. preventing longitudinal movement of the instrument).

Preferably, the stereoguide further comprises a second clamp having a clamping position on the axis of insertion and on the opposite side of the guide elements to the first clamp for clamping instruments passing through the guide elements. It is also preferred that the or each clamp is movable away from its clamping position and most preferred that the or each clamp is swivelable away from its clamping position.

It is preferred that the second clamp is disposed between the guide elements and the target. In such a case, it is further preferred that the stereoguide include a post extending from the first guide element and carrying the first clamp, and a leg extending from the second guide element and carrying the second clamp, wherein the second guide element is closer to the target than the first guide element.

According to a second aspect of the invention, there is provided a method of positioning an instrument at a target using a stereoguide according to the first aspect of the invention, the method comprising inserting a wire into a support tube; inserting the wire and support tube together along an axis of insertion towards the target via the guide elements of the stereoguide; removing the support tube form the wire, leaving the wire in situ; inserting a guide tube around the wire towards the target; securing the guide tube in position; removing the wire; inserting the instrument to the target via the guide tube.

Preferably the support tube has a stop at its proximal end (i.e. the end that is not inserted) which abuts a guide element preventing any further insertion of the support tube.

It is preferred that the inserting of the wire into the support tube results in the wire projecting from the end of the support tube. It is most preferred that the wire projects from the support tube towards the target by about 25 mm.

Another preferred feature is that, once the wire is inserted into the support tube they are fixed together by virtue of a finger tightenable screw carried by the support tube. The finger tightenable screw may form part of the stop referred to above. After inserting the wire to the target, it is advantageous for the first clamp to be clamped to the wire whereby the wire is held securely.

It is preferred that removal of the support tube included release of finger tightenable screw. According to a preferred embodiment, removal of the support tube includes moving the support tube along the wire until it is positioned between the first and second clamps, clamping the wire with the second clamp when the second clamp is between the target and the guide elements, releasing the first clamp and withdrawing the support tube from the wire. Preferably, the step of inserting the guide tube includes passing the guide tube over the wire until the tube is positioned between the first and second clamps, clamping the wire with the first clamp, releasing the second clamp and moving the guide tube towards the target. Finally, before removing the wire, both clamps are released.

Embodiments of the present invention will be described by way of example only with reference to the drawings in which:

FIG. 1 is a view of a catheter for use with the stereoguide according to the present invention;

FIG. 2 is a view showing part of the catheter of FIG. 1 with internal features shown in dotted lines;

FIG. 3 is an end view of the catheter from the left hand end of FIG. 2;

Figures 4, 5:
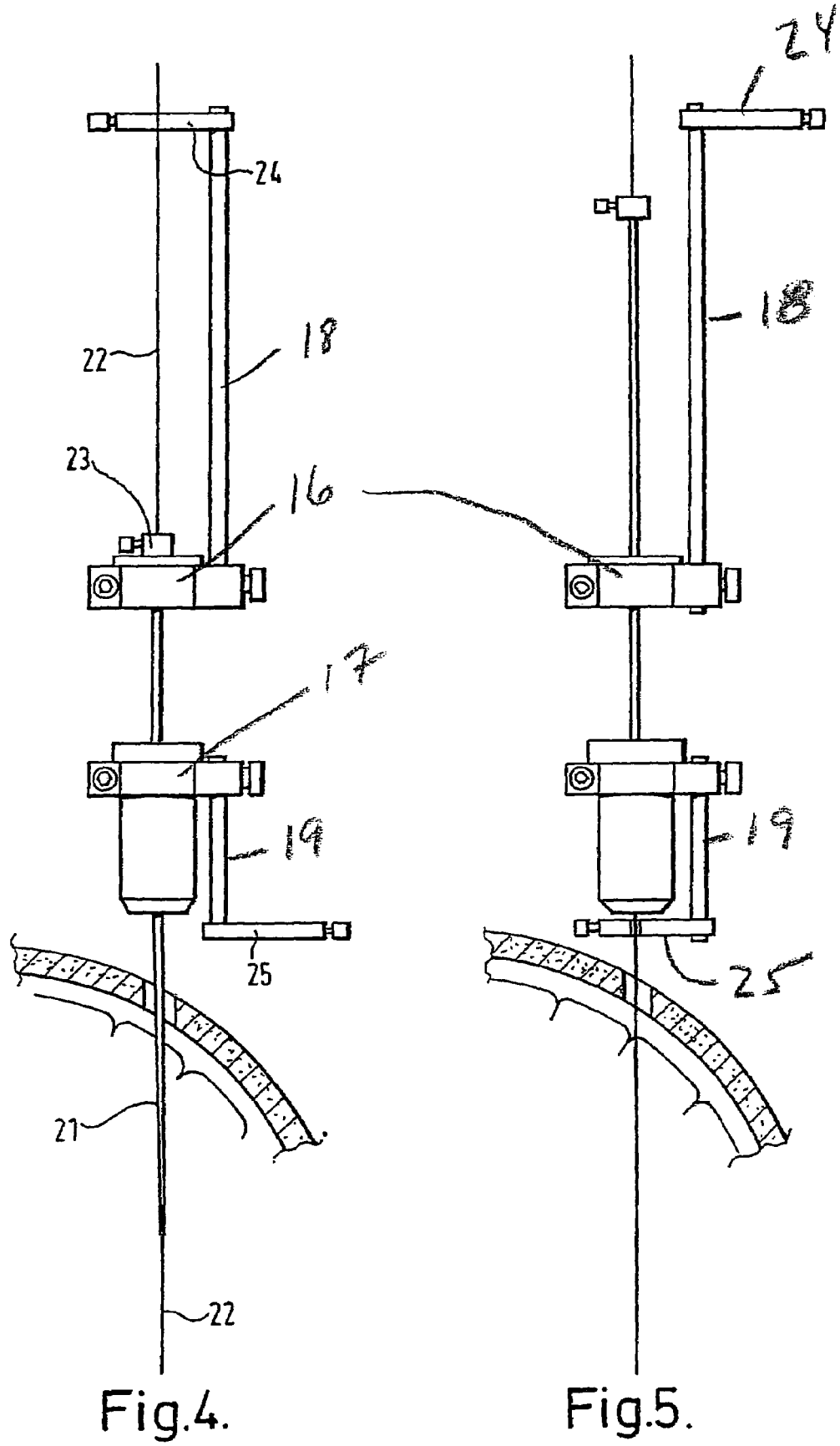
FIG. 4 shows a first phase of stereotactic insertion.
FIG. 5 shows a second phase of stereotactic insertion.

As is explained above, the accuracy of insertion of an instrument is crucially important.

EXAMPLE 1

FIGS. 1, 2 and 3 show a catheter 1 suitable for use with the stereoguide of the present invention. The catheter 1 includes a length of fine tubing 2, the outer diameter of which is no more than 1 mm, and most preferably no greater than 0.7 mm. It is even more preferred that the outer diameter be no more than 0.5 mm. In this instance, the catheter tubing 2 is constructed from polyurethane plastic and preferably from carbothane 55DB20 (Thermedics Polymer Products, Woburn Mass., USA). The fine tubing 2 is linked to a length of connector tubing 3 via a hub 4. The connector tubing 3 is, in this case, made from polyurethane plastic, such as carbothane 85AB20, although other materials could also be used.

The hub 4 in this case is also constructed using polyurethane, such as carbothane 72DB20. Again, other materials may also be appropriate.

The fine tubing 2 is intended to be inserted into the brain of a patient, whereas the connector tubing 3 is intended to lead to a pump by which a therapeutic agent may be pumped intermittently or continuously to a desired brain target. For long term drug delivery, the pump would be implanted subcutaneously and the reservoir refilled as necessary percutaneously through a palpable port. In this case, the connector tubing 3 would also be inserted subcutaneously.

The hub 4 includes a central body 5, which is generally cylindrical and a pair of diametrical opposing wings 6 each containing a countersunk hole whereby the hub may be screwed to the outer surface of the skull of the patient.

The cylindrical body 5 of the hub 4 includes a passageway passing through its complete length. The passageway includes a first narrow passage 8 of uniform diameter into which the fine tubing is inserted and securely held. The passageway also includes a second wide passage 9 of uniform diameter into which the connector tubing 3 is inserted and securely held. Between the first and second passages 8, 9 is a third linking passage 10 which is generally tapered in order to take account of the different internal diameters of the fine tubing 2 and the connector tubing 3. It will be noted that the ends of the third passage 10 are of the same or very similar diameter to the internal diameters of the fine tubing 2 and the connector tubing 3.

From FIG. 2, it can be seen that the right hand end of the hub 4 is frustoconical, and the end of the hub is planar and forms a stop 11, the significance of which will be understood from the description below.

The insertion of the catheter will now be described. Firstly, a stereotactic frame is attached to the patient's skull and the position of the intracranial target is identified by imaging the patient wearing the stereotactic frame and defining the position of the target as a three dimensional co-ordinate. This is a standard technique within the field of neurosurgery and suitable stereotactic frames are available from Elekta Instruments AB.

In this insertion technique, a number of phases or steps are taken which are shown in FIGS. 4 to 7. As will be appreciated, small diameter catheters have a tendency to drift off the planned trajectory during insertion as a result of the flexibility inherent in a small diameter instrument. Since neurosurgical targets are often deeply situated, typically 70-80 mm from the surface of the skull, and sometimes as much as 100 mm from the skull surface, the catheter must normally be very rigid, and therefore of a larger diameter.

Examples of possible targets include targets in the mesencephalon including the subthalamic nucleus, the substantia nigra and the pedunculor-pontine nucleus. The mesencephalon is a critical region of the brain where is it is important to minimise trauma from the passage of an electrode or catheter. It is typically at a depth of about 70-80 mm from the skull surface and is contained within a volume which has a height of approximately 20-25 mm.

In FIGS. 4 to 7, a stereoguide according to the present invention is shown in use during the insertion of an instrument. Stereoguides are carried by a stereotactic frame which is securely attached to the skull of the patient. The stereoguide can be adjusted on the stereotactic frame in order to be positioned very accurately to direct a surgical instrument to the desired position. Whereas stereoguides normally include two guide elements, the stereoguide in FIGS. 4 to 7 also includes additional clamps. Although the stereotactic frame is not shown in FIGS. 4 to 7, it will be appreciated that the stereoguide is carried by the frame. The stereoguide includes an upper guide element 16 and a lower guide element 17 which are alignment in order to define the path of any instrument being positioned in the brain of a patient. A post 18 extends upwardly from the upper guide element, the top of which carries an upper clamp 24. A leg 19 extends downwardly from the lower guide element and carries a lower clamp 25 at its lower end. Both upper and lower clamps may be swivelled to and from positions where they will meet the axis of the stereoguide. For example, is will been seen in FIG. 4 that the upper clamp 24 is in alignment with the axis of the stereoguide, whereas the lower clamp 25 is not. The opposite position is shown in FIG. 5.

From the foregoing, it will be appreciated that the stereoguide has as its purpose the longitudinal guidance of instruments towards a target within the brain. It defines an axis along which the instruments are inserted so that, provided there is no deviation of the instrument caused by flexing during insertion, the instrument will be very accurately directed towards the target.

It will also be understood from the introduction to this application that the target is the point within the brain which is to be treated by the instrument, and to which the instrument is directed by the stereoguide. The instruments that are intended to be inserted include catheters for delivery of therapeutic agents, electrodes for delivering electric pulses, guide tubes which are inserted into the brain and through which other instruments may be passed, and wires which may be used to rigidify tubular instruments inserted into the brain or guide tubular instruments to a target in the brain. The clamps have as their primary function the securing of instruments during insertion or removal so as to prevent them from moving longitudinally along the axis of insertion.

To facilitate insertion of fine instruments into mesencephalic targets, insertion takes place as follows.

Firstly, a small diameter tungsten guidewire 22 of 0.6 mm in diameter is inserted in a tube 21 with an outer diameter of 1.7 mm and fixed within the tube 21 with a finger-tightened grub screw 23 such that the wire 22 protrudes from the distal end of the tube 21 by 25 mm. The tube 21 and wire 22 can be seen in FIG. 4 showing the first phase of insertion in which the tube 21 with the wire 22 projecting from its end can be seen. The finger tightened grub screw 23 can be seen at the top (i.e. the proximal end) of tube 21, in which the wire 22 is held. The proximal end of the tube 21 also comprises a stop which abuts a guide element on insertion. The distal end of the tube 21 is tapered over 20 mm, and the tube 21 has a stop at its proximal end.

Insertion takes place from a stereotactic frame in which the target has been identified and defined in terms of three dimensional co-ordinates. The stereotactic frame carries a stereoguide according to the present invention. During the first phase of insertion shown in FIG. 4, the tube and wire are together lowered towards the target. In this case, the tube is 165 mm in length from the stop to the distal end, and since the tube 21 and the wire are inserted as a unit, the distance from the stop of the tube to the tip of the guidewire 22 is 190 mm. The wire 22 extends above the top of the tube by approximately 150 mm. The upper clamp 24 and the lower clamp 25, can be swivelled to positions of engagement with the wire, tube or instrument which is being inserted or removed.

Once the guidewire 22 has reached its target, the upper clamp 24 is swivelled to clamp the proximal end of the guidewire 22. This prevents longitudinal movement of the wire. Once the grub screw 23 has been loosened, the tube 21 can be withdrawn from the brain leaving the wire 22 in situ. Once the tube 21 has been raised up towards the upper clamp, the lower clamp can be swung across to clamp the now exposed wire 22, and the upper clamp 24 can be released, as shown in FIG. 5. This allows the tube 21 to be removed altogether from the top of the wire 22.

A guide tube 31 is threaded onto the wire 22, and the upper clamp 24 is then swung around and closed on the wire 22. The lower clamp 25 can then be released to allow the guide tube 31 to be inserted into the brain so that its distance is approximately 1 or 2 cm short of the target, also shown in FIG. 7. The guide tube 32 has at its upper end a head with a threaded outer surface which permits the head to be screwed into the tapped burrhole in the patient's skull, thereby securing the guide tube 31 securely in position.

Figures 6, 7:
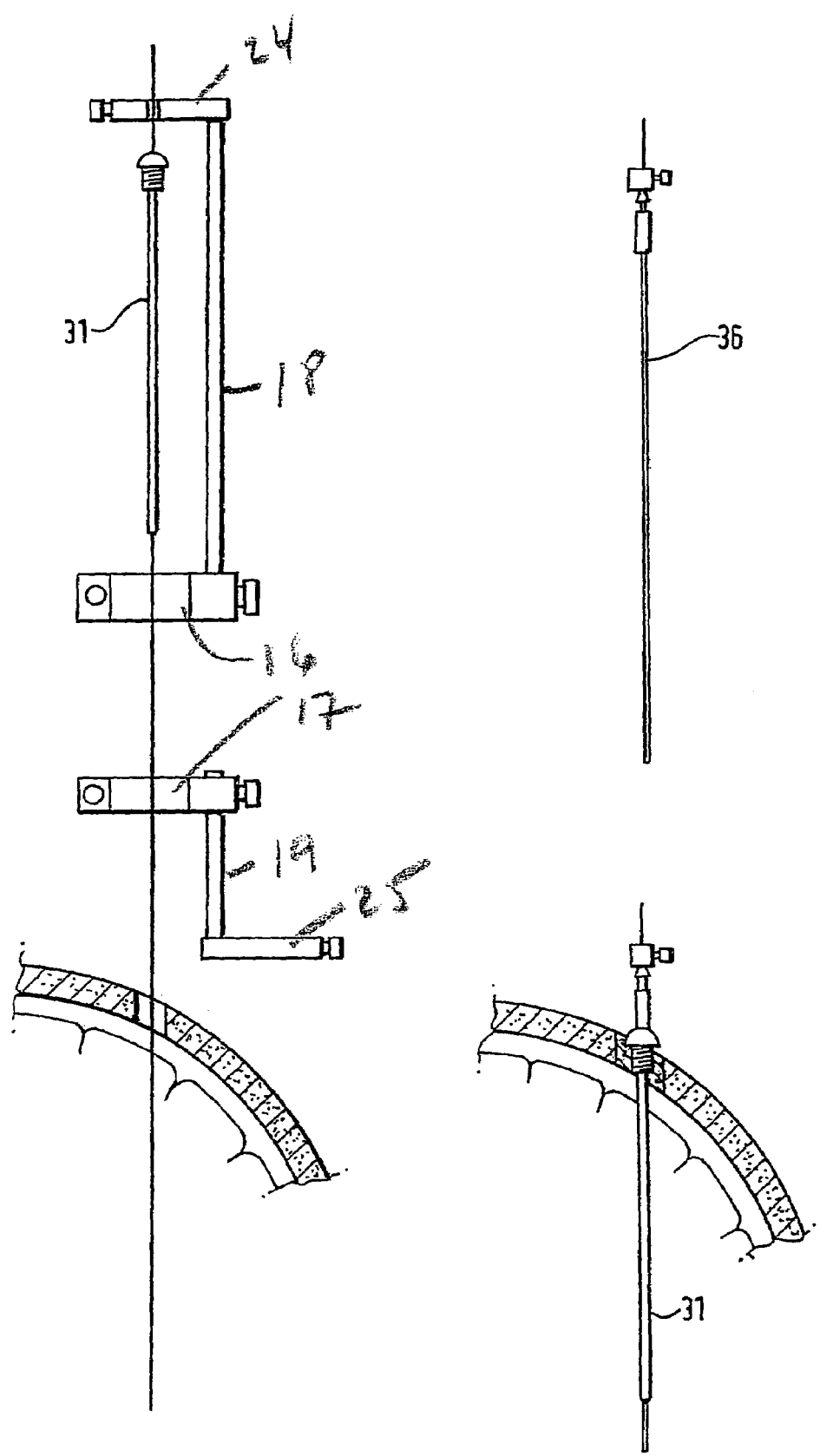
FIG. 6 shows a third phase of stereotactic insertion.
FIG. 7 shows a fourth phase of stereotactic insertion.

Once the guide tube 31 is installed, the guidewire 22 may be removed and FIG. 7 shows that a 0.65 mm catheter 36 can then be inserted down the guide tube 31 to the target. Alternatively other instruments can be inserted at this point, such as an electrode.

This method has the particular advantage that, on the first pass, the guidewire being stiffened by the tube 21 will hit the target, and then by inserting a guide tube short of the target, the brain target will be fixed and the guide tube will facilitate the insertion of a very fine instrument to the target. For the treatment of certain conditions such as Alzheimer's disease it is necessary to deliver nerve growth factors to targets in the nucleus basalis through several in-dwelling catheters. If each catheter is only 0.65 mm in diameter, multiple fine catheters can be inserted without substantially disrupting the tissue it is intended to regenerate.

To insert a DBS electrode, a similar technique can be used. When the DBS electrode is not tubular (i.e. it has a closed end), it is preferred that a 1.3 mm electrode or guide rod is used to place a guide tube just short of the target. The DBS electrode is then subsequently inserted down the guide tube, once the electrode or guide rod has been removed. Alternatively, the DBS electrode is tubular (i.e. has open ends), a straight wire can be guided to the target and the electrode introduced around the wire.

All document cited above are incorporated herein by reference.

The invention claimed is:

1. A method of positioning an instrument at a target using a stereoguide, the stereoguide comprising first and second guide elements spaced relative to each other through which instruments are passed along an axis of insertion towards a target; characterized by a first clamp having a clamping position on the axis between the guide elements and the target and a second clamp having a clamping position on the axis of insertion and on the opposite side of the guide elements to the first clamp for clamping instruments passing through the guide elements, said method comprising;
  inserting a wire into a support tube;
  inserting the wire and support tube together along an axis of insertion towards the target via the guide elements of the stereoguide;
  once the wire is inserted into the support tube they are fixed together by virture of a finger tightenable screw by the support tube;
  removing the support tube form the wire, leaving the wire in situ;
  inserting a guide tube around the wire towards the target;
  securing the guide tube in position;
  removing the wire; and
  inserting the instrument to the target via the guide tube.

2. A method according to claim 1, wherein the insertion of the wire into the support tube results in the wire projecting from the end of the support tube.

3. A method according to claim 2, wherein the wire projects from the support tube towards the target by about 25 mm.

4. A method according to claim 1, wherein after insertion of the wire to the target, the first clamp is clamped to the wire.

5. A method according to claim 1, wherein removal of the support tube includes release of the finger tightenable screw.

6. A method according to claim 5, wherein removal of the support tube includes moving the support tube along the wire until it is positioned between the first and second clamps, clamping the wire with the second clamp, releasing the first clamp, and withdrawing the support tube from the wire.

7. A method according to claim 1, wherein insertion of the guide tube includes passing the guide tube over the wire until the tube is positioned between the first and second clamps, clamping the wire with the first clamp, releasing the second clamp, and moving the guide tube towards the target.

8. A method according to claim 1, wherein, before removing the wire, both clamps are released.

9. A method of positioning an instrument at a target using a stereoguide, the stereoguide including first and second guide elements spaced relative to each other through which instruments are passed along an axis of insertion towards a target; characterized by a first clamp having a clamping position on the axis between the guide elements and the target and a second clamp having a clamping position on the axis of insertion and on the opposite side of the guide elements to the first clamp for clamping instruments passing through the guide elements, said method comprising;
  inserting a wire into a support tube;
  inserting the wire and support tube together along an axis of insertion towards the target via the guide elements of the stereoguide;
  once the wire is inserted into the support tube they are fixed together by virture of a finger tightenable screw by the support tube;
  removing the support tube form the wire, leaving the wire in situ;
  inserting a guide tube around the wire towards the target;
  securing the guide tube in position;
  removing the wire; and
  inserting the instrument to the target via the guide tube and after insertion of the wire to the target, the first clamp is clamped to the wire.

* * * * *